May 16, 1933. L. BURBANK Plant Pat. 65
ROSE
Filed June 30, 1932
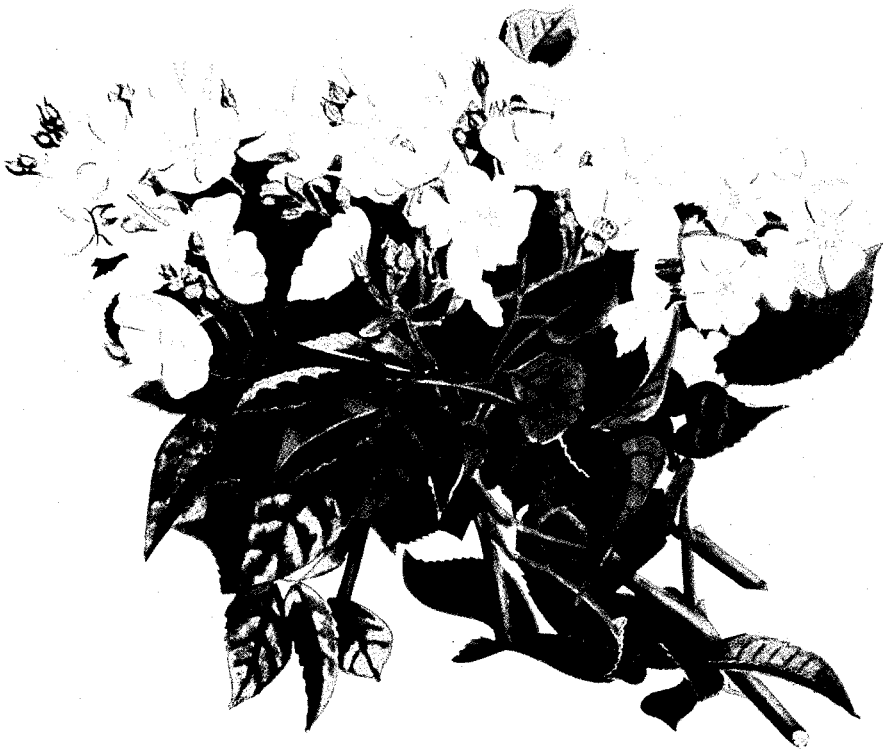
Inventor:
ELIZABETH WATERS BURBANK
EXECUTRIX OF THE ESTATE
OF LUTHER BURBANK, DECEASED,
By Robb & Robb,
Attorneys Patented May 16, 1933

Plant Pat. 65

UNITED STATES PATENT OFFICE

LUTHER BURBANK, DECEASED, LATE OF SANTA ROSA, CALIFORNIA, BY ELIZABETH WATERS BURBANK, EXECUTRIX, OF SANTA ROSA, CALIFORNIA, ASSIGNOR TO STARK BRO'S NURSERIES & ORCHARDS COMPANY, OF LOUISIANA, MISSOURI

ROSE

Application filed June 30, 1932. Serial No. 620,228.

The invention relates to a new variety of rose of the pillar-rambler type, the novel characteristics of which reside particularly in the unique color, vigorousness of growth, and cluster habit of growth, as well as in other features which will be hereinafter more fully pointed out and described.

The present rose is apparently a hybrid of *Rosa rugosa* and *Rosa multiflora*, certain features of these parents being apparent and similar, and other features being quite dissimilar from the parents or any other rose, these differences and dissimilarities being such as to indicate the newness and distinctness of variety of the rose which has been asexually reproduced to show constancy of the features.

For example, *Rosa rugosa* is characterized by thick, leathery, dark green, crinkly foliage and with thickly set slender spines, persistent to the terminal tips of each branch. The plant as a whole is of shrub type of growth, producing umbel-like terminal flower clusters composed usually of only from four to six blossoms which are followed by large orange-red hips or fruits, frequently one-half to three-fourths of an inch in diameter.

In comparison, the new rose has somewhat the same heavy, dark green, crinkly foliage, the older stems being thickly set with spines of varying length, while the new flowering stems are almost entirely devoid of spines. The flowers are materially different and entirely distinct in color and form and are borne in large, composite, rather compact panicled clusters of from twelve to fifty flowers or blossoms to each cluster as distinguished from the umbel-like arrangement and few flowered clusters of the *Rosa rugosa*. The plant is of vigorous, pillar-rambler habit of growth as differing from the well known bush form of *Rosa rugosa*. The hips or fruits are small, averaging approximately one-fifth of an inch in diameter, spherical in outline, red in color and somewhat resembling holly berries, but differing entirely in form, size and color from the fruits of *Rosa rugosa*.

The nearest known approach of the rose generally to the Multiflora type is the hybrid Multiflora known as the "American Pillar" rose, although there is but slight similarity in flower formation. The "American Pillar" rose has much the same habit of vegetative growth as the new rose. The flower petals of "American Pillar" are arranged in a single tier and are bright pink in color, blending to white at the base and enclosing a large cluster of bright yellow stamens. The flowers are disposed in rather loosely clustered panicles and are followed by hips or fruits that are ovate in shape, averaging one-half in length and three-tenths of an inch in width. The canes are rather sparsely studded with coarse, stiff, recurved spines approximately three-tenths of an inch in length. Typical leaves are generally composed of eight lateral and one terminal leaflets, all of which have rather coarsely serrate margins.

On the other hand, the rose differs from the "American Pillar" in that the flowers are borne in huge, rather compactly clustered panicles, the individual flowers averaging approximately one and one-half inches in diameter with the petals arranged in a single tier. A plant in full bloom from a distance somewhat resembles a mass of rhododendrons. The petals are rather crinkly along their outer edges and have a tendency to curve inwardly toward the center of the flower, thereby giving to the flower a unique and artistic shallow bowl appearance even when fully expanded. The newly opened flower petals are a deep, clear, apple blossom pink, blending gradually to a pure white at the base of the petals, the flower developing a faint bluish-rose tinge at the outer petal tips with age as the flower expands fully. The soft blending of colors of the newly expanded and of the older flower produces in the huge flower cluster a toning of unusually interesting iridescent variation that is so elusive as to be difficult of description. The hips or fruits of this rose are spherical and the canes are thickly set with varying lengths of from minute prickles to spines two-tenths of an inch in length, as compared with the aforementioned varieties. The typical leaves are generally composed of six lateral and one terminal leaflets with finely serrate margins. The huge flower clusters are so numerous as to practically obscure the foliage beneath.

One of the very important and particularly noticeable features of this new rose resides in the blooming of the flowers as the leaves and putting on and before the leaves become large enough to hide any of the blooms. That is to say, the blooming sufficiently precedes the foliage so as to present a clear vision of all the blooms as distinguished from putting out leaves first and then blooming as the case of the known climbers. In the new rose, a bloom stem is put out from almost every eye first.

The foregoing comparisons have been made for the purpose of indicating the nearest approach in vegetative qualities, flower and form to any known rose variety. It is to be understood, however, that differences in addition to those specifically mentioned exist, it being the purpose of the foregoing to point out the most prominent and outstanding distinctions.

A still further important feature which sets this rose apart from other roses of this type is the mildew resistant characteristic which exists even in climates where other roses mildew badly.

For the purpose of presenting a concise description of the new variety, the following summary is set forth:

*Plant:—*

*Growth.*—Vigorous climbing habit, with strong nearly straight or slightly sinuous canes frequently as large as one inch in diameter and fourteen feet long.

*Bark.*—Thick, firm, but not very tough or fibrous, dark green or partly liver brown in color on canes of current season's growth, modified by faint grayish lines lengthwise and showing considerable cress green undercolor toward the tips of the new growth, the older bark becoming rough woody and dull gray with age.

*Foliage:—*

Very abundant and strong, the leaves being very large and somewhat similar in shape to those of Crimson Rambler but much larger, leaflets averaging one and one-quarter inches wide by two and one-quarter inches long.

*Texture.*—Thick and surface rugose but not what would be considered crumpled; free from mildew though under the same conditions as other plants which heavily mildew.

*Color.*—Very dark green and luxuriant, much darker than Crimson Rambler.

*Leaflets.*—Vary from five to seven, usually seven.

*Climbers:—*

Extra-thrifty grower; heavy strong weeping canes three-eights to nine-sixteenths of an inch in diameter at a point two inches above base and larger than ordinary all the way up to the tips; canes start upwardly and then curve over rainbow-shaped until most of the tips almost touch the ground, the highest point of the bow being two to three feet above the ground, more upright than Crimson Rambler.

*New shoots.*—Very heavy and rapid growing, almost covered with short and medium length bristles intermingled with a few short thorns.

*Flowering shoots.*—Steady growth, relatively large at the base, tapering rapidly to rather slender branching flower stems; generally free from thorns but bear numerous short blunt prickles on the smaller stems and pedicels; each flower shoot bears several dormant buds near the base.

*Internodes:—*

Short.

*Thorns:—*

Large, slightly recurved, generally two to the node on the larger canes and a little below and to each side of the buds; between the large thorns, the cane is covered with an abundant mass of short, blunt very small thorns or supple modified bristles or spines, completely covering the canes from base to tip except for certain areas appearing with no particular regularity where the bark is free from bristles and prickles.

*Color.*—Large thorns cinnamon buff to reddish or clay, becoming dull gray with age; small thorns or bristles or prickles yellowish-gray.

*Dormant buds:—*

Large, plump, round-conical in form, with points almost at right angles to the cane.

*Color.*—Nearly ox-blood red with slight yellowish tinge toward the leaf-scar; with favorable exposure every bud on the new growth produces a flower cluster.

*Blooms:—*

Very profuse and free flowering, with uniform medium to large clusters on stems up to fifteen inches long; early blooming and long season but not as long season as that of double-flowered ramblers; blooming about two weeks earlier than Crimson Rambler grown under comparable conditions, shedding its blooms as Crimson Rambler is beginning to bloom; cluster of blooms produced from almost every eye on the cane from near the base to the tip, averaging about twenty-five blooms to the cluster.

*Florets.*—Generally five petals, single, cupped, one and one-quarter to one and one-half inches across; petals crinkled like those of *Rosa rugosa.*

*Color.*—Bright, almost salmon pink in newly opened flowers, shading to white at the base, giving apple blossom effect. Large, bright yellow stamens in newly opened flowers give flowers a golden-center appearance, but generally no other tendency to yellow coloring. A bluish cast blending with the pink and yellow creates a most unique and artistic appearance.

*Petal persistence.*—Petals fall promptly, leaving the clean ornamental foliage effect of the leaves and new growth.

*Fruit or hips:*—

Few; small, spherical, averaging one-eighth to one-quarter of an inch in diameter, containing a few medium sized rounded yellow seeds.

*Color.*—Ox-blood red.

Having set forth the most notable features of the invention, it is apparent that the rose is clearly endowed with individual identity and is characterized truly as a new and distinct variety as manifested particularly in its floral coloring, individuality in foliage, formation of the component parts of the plant, and habit of growth. Owing to its vigorousness, profuse cluster flowering characteristic, its peculiar habit of blooming before the leaves attain such size as might tend to hide a portion of the blooms, and the subsequent prompt falling of the petals, leaving the clean ornamental foliage effect of the leaves and the new growth, it is excellently adapted for use as a hedge as well as for the usual and ordinary purposes of a rambler rose.

What is claimed as new is:—

A new and distinct variety of rambler rose characterized particularly by vigorousness and form of plant growth, profuseness of and cluster blooming habit, unique foliage and floral coloring and form, and relation of blooming period to foliation, as herein shown and described.

In testimony whereof I affix my signature.

ELIZABETH WATERS BURBANK,
*Executrix of the Estate of Luther Burbank, Deceased.*